United States Patent [19]
Aebersold et al.

[11] Patent Number: 5,856,082
[45] Date of Patent: Jan. 5, 1999

[54] DEVICES AND METHODS FOR CHARACTERIZING PROTEINS AND PEPTIDES

[75] Inventors: Rudolf H. Aebersold, Mercer Island, Wash.; Lawrence N. Amankwa, Surrey, Great Britain

[73] Assignee: University of British Columbia, Vancouver, Canada

[21] Appl. No.: 299,290

[22] Filed: Aug. 31, 1994

[51] Int. Cl.$^6$ .............................. C12Q 1/00; G01N 30/02
[52] U.S. Cl. ................. 435/4; 435/7.1; 435/7.5; 435/15; 435/21; 435/68.1; 435/97; 435/287.9; 435/288.6; 422/70; 204/452; 204/603; 250/288
[58] Field of Search .................................. 422/70; 436/86, 436/89, 161, 173; 435/4, 6, 7.1, 7.5, 15, 21, 68.1, 97, 287.1, 287.9, 288.6; 204/603, 452; 250/288

[56] References Cited

U.S. PATENT DOCUMENTS

| | | | |
|---|---|---|---|
| 4,705,616 | 11/1987 | Andresen et al. | 204/299 R |
| 4,994,165 | 2/1991 | Lee et al. | 204/299 R |
| 5,003,059 | 3/1991 | Brennan | 536/27 |
| 5,066,785 | 11/1991 | Miller | 530/345 |
| 5,131,998 | 7/1992 | Jorgenson et al. | 204/299 R |
| 5,137,695 | 8/1992 | Rusnak et al. | 422/116 |
| 5,202,010 | 4/1993 | Guzman | 204/299 R |
| 5,240,577 | 8/1993 | Jorgenson et al. | 204/180.1 |
| 5,389,221 | 2/1995 | Jorgenson et al. | 204/299 R |
| 5,449,064 | 9/1995 | Hogan et al. | 204/180.1 |
| 5,496,460 | 3/1996 | Jorgenson et al. | 204/604 |
| 5,516,698 | 5/1996 | Begg et al. | 436/89 |

OTHER PUBLICATIONS

Amankwa and Kuhr, "Trypsin–Modified Fused–Silica Capillary Microreactor for Peptide Mapping by Capillary Zone Electrophoresis," *Anal. Chem.* 64: 1610–1613, 1992.

Smith et al., "New Developments in Biochemical Mass Spectrometry: Electrospray Ionization," *Anal. Chem.* 62: 882–899, 1990.

Huddleston et al., "Collisional Fragmentation of Glycopeptides by Electrospray Ionization LC/MS and LC/MS/MS: Methods for Selective Detection of Glycopeptides in Protein Digests," *Anal. Chem.* 65: 877–884, 1993.

Palczewski et al., "Identification of the Autophosphorylation Sites in Rhodopsin Kinase," *Journal of Biological Chemistry* 267(26): 18991–18998, 1992.

Thompson et al., "Capillary Electrophoresis/Electrospray Ionization Mass Spectrometry: Improvement of Protein Detection Limits Using On–Column Transient Isotacophoretic Sample Preconcentration," *Anal. Chem.* 65: 900–906, 1993.

Burlingame et al., "Mass Spectrometry," *Anal. Chem.* 64: 467R–502R, 1992.

Caprioli et al., "Continuous–Flow Sample Probe for Fast Atom Bombardment Mass Spectrometry," *Anal Chem.* 58: 2949–2954, 1986.

Moseley et al., "Optimization of a Coaxial Continuous Flow Fast Atom Bombardment Interface between Capillary Liquid Chromatography and Magnetic Sector Mass Spectrometry for the Analysis of Biomolecules," *Anal. Chem.* 61: 1577–1584, 1989.

Emary et al., "Liquid Chromatography/Time–of–Flight Mass Spectometry with High–Speed Integrated Transient Recording," *Anal. Chem.* 62: 1319–1324, 1990.

(List continued on next page.)

*Primary Examiner*—David A. Redding
*Attorney, Agent, or Firm*—Seed and Berry LLP

[57] ABSTRACT

The present invention provides analytical devices for the characterization of the primary structure of proteins and peptides, comprising a microenzyme reactor, a separation device, an interface between the microenzyme reactor and the separation device, a mass spectrometer, and an interface between the separation device and the mass spectrometer. Also provided are methods for characterizing a protein or peptide utilizing such devices.

42 Claims, 5 Drawing Sheets

OTHER PUBLICATIONS

Carr and Biemann, "Identification of Posttranslationally Modified Amino Acids in Proteins by Mass Spectrometry," *Methods in Enzymology* 106: 29–59, 1984.

Nashabeh and Rassi, "Enzymophoresis of nucleic acids by tandem capillary enzyme reactor–capillary zone electrophoresis," *Journal of Chromatography* 596:251–264, 1992.

Cobb and Novotny, "High–Sensitivity Peptide Mapping by Capillary Zone Electrophoresis and Microcolumn Liquid Chromatography, Using Immobilized Trypsin for Protein Digestion," *Anal Chem.* 61: 2226–2231, 1989.

Wheat et al., "Use of Capillary Electrophoresis for the Detection of Single–Residue Substitutions in Peptide Mapping," *J. Liq. Chromatogr.* 14: 987–996, 1991.

SCHEME FOR IMMOBILIZATION OF ENZYMES ONTO
FUSED SILICA CAPILLARY

Fig. 1

CROSS SECTION OF FUSED SILICA CAPILLARY ENZYME REACTOR

DEVICES AND METHODS FOR CHARACTERIZING PROTEINS AND PEPTIDES

DESCRIPTION

1. Technical Field

The present invention relates generally to devices and methods for characterizing proteins and peptides and, more specifically, to an integrated approach for characterization of the primary structure of nanogram and picogram quantities of proteins and peptides.

2. Background of the Invention

Proteins are naturally occurring compounds that are composed of long chains of amino acids. Briefly, proteins are found throughout living systems in the form of hormones, structural elements, enzymes, immunoglobulins and other constituents of living things. Due to their central importance in living systems, the structure and function of proteins is widely studied.

For example, study of the primary structure of proteins (i.e., the amino acid sequence of individual proteins) can reveal subtle differences between similar individual proteins. Such information is useful for detecting post-translational processing resulting from proteolysis, identifying and localizing genetic variants, and controlling the quality of genetically engineered protein products.

Although the process by which amino acids are assembled into a polypeptide chain in a sequence is predetermined by a gene's nucleic acid code is well understood, prediction of the exact primary structure of the final protein product resulting from such a process is not always accurate. Such inaccuracy results, for example, from the incorporation of chemical groups into the polypeptide after the polypeptide has been assembled (i.e., post-translational modification). To date, more than one hundred types of post-translational modifications have been identified as constituents of different proteins from a variety of sources. Thus, although only twenty primary amino acids are specified in the genetic code, numerous chemical derivatives of the primary amino acids exist and appear in a final protein product and are important for the structure and function of the protein.

The appearance of these modified amino acid residues in a final protein product cannot be predicted a priori from the nucleic acid code. In many instances, these modifications alter bioactivity and three-dimensional structure of a protein and also play a significant role in protein transport from the site of protein synthesis to the final biological destination.

Generally, post-translational modifications may be classified into four groups, depending upon the site of chemical modification of the protein. In particular, protein modifications may involve (1) the carboxylic acid group of the carboxy terminal amino acid residue, (2) the amino group of the amino terminal amino acid residue, (3) the side chain of individual amino acid residues in the polypeptide chain, and/or (4) the peptide bonds in the polypeptide chain. The modifications may be further subgrouped according to distinct types of chemical modifications, such as phosphorylation, glycosylation, acylation, amidation and carboxylation.

Determination of the site of a post-translational modification in a protein or peptide may pose significant problems. For example, phosphorylated amino acids can not be readily detected at high sensitivities without the use of radioisotopes when conventional techniques such as protein sequence analysis are utilized. Other techniques for analysis such as in vivo incorporation of radioactive phosphorous ($^{32}p$) into the protein followed by protein isolation, fragmentation, separation of the resulting peptides and detection by autoradiography have drawbacks such as requiring extremely large quantities of radioactive phosphorous (Palczewski et al., *J. Biol. Chem.* 267:18991–98, 1991) and the fact that no structural information is obtained. Typically, the quantity of radioactive material required may exceed those levels ordinarily permitted for a particular laboratory, and more importantly, such radioactive material presents a substantial health and environmental hazard.

Mass spectral techniques in general, and tandem mass spectrometry (MS/MS) in particular, have also been used to probe post-translational modifications in proteins. Briefly, in this technique, parent molecular polypeptide ions are fragmented into daughter ions which are selected and further fragmented to yield information relating to the nature and site of the modification. This technique, however, has several drawbacks, including the expense and complexity of the MS/MS instrumentation and the limitation of its inability to distinguish the nature of equivalent mass fragments. For example, the mass spectrometer's inability to distinguish equivalent mass fragments (i.e., hexoses, $C_6H_{12}O_6$) precludes the usefulness of this technique for glycoprotein characterization in which the type of sugar attached to a particular amino acid residue needs to be identified.

By their nature, proteins are complex compounds and therefore complete structural characterization requires a combination of chemical, enzymatic, and instrumental techniques. Typically, protein characterization first requires protein isolation followed by either chemical or enzymatic digestion of the protein into smaller peptide fragments. Once the protein has been at least partially digested, the peptide fragments are separated by gel electrophoresis, liquid chromatography, or a two-dimensional approach (e.g., electrophoresis-thin layer chromatography) to obtain a peptide map. Ultimately, the peptide fragments are analyzed and their amino acid sequence determined instrumentally.

Despite the importance of determining the amino acid sequence of peptide fragments, current techniques suffer from several drawbacks. For example, complete protein structure determination is typically limited by the quantity of protein available for analysis. Thus, when the quantity of protein available for testing is present in only very limited quantities, analysis and characterization of the protein is either impracticable or time consuming, expensive, and labor intensive.

In order to overcome the problem of limited sample, protein analyses have recently been directed toward analytical techniques with increased sensitivity. Often, more than a single analytical technique is combined to provide the analytical sensitivity required. These combined analytical techniques are generally referred to as tandem techniques.

For example, traditional separation techniques such as liquid chromatography and slab gel electrophoresis have been replaced with techniques such as capillary electrophoresis (CE), which has found success as the separation tool of choice for the resolution of biomaterials such as proteins and oligonucleotides. In order, however, to detect the relatively small quantity of materials separated by CE, highly sensitive detection techniques are required. While the most common detection systems are based on optical absorbance, other sensitive detection techniques have also been attempted, including fluorescence and mass spectrometric detection techniques.

Proteins have been analyzed by the tandem technique of CE-fluorescence detection, in order to couple a high resolution CE separation technique with high sensitivity fluorescence detection. In particular, at least one group has attempted to analyze tryptic digests of casein by capillary zone electrophoresis followed by their detection under laser-induced fluorescence (Amankwa and Kuhr, *Anal. Chem.* 64:1610–1613, 1992). Capillary electrophoretically separated proteins have also been identified by electrospray ionization mass spectrometry (Karger et al., *Anal Chem.* 65:900–906, 1993).

In addition to proteins, nucleic acid molecules have also been analyzed by sequential enzymatic digestion, resolution and detection of the enzyme products. For example, in one technique which is referred to as the enzymophoresis of nucleic acids by tandem capillary enzyme reactor-capillary electrophoresis (Nashabeh et al., *J. Chromatogr.* 596:251–264, 1992), a nucleic acid sample was exposed to an enzyme reactor composed of ribonuclease T1, hexokinase and adenosine deaminase immobilized on the inner wall of a short fused silica capillary. The enzyme-modified capillary reactor was coupled in series (end to end) with a capillary zone electrophoresis separation capillary. The technique facilitates on-line digestion and mapping of minute amounts of transfer ribonucleic acids, as well as the simultaneous synthesis and separation of nanogram quantities of oligonucleotides.

In the practice of that technique, however, the reactor is required to be uncoupled from the separation capillary once the digestion of the sample is completed, and the analysis of the enzymatic reaction products is subsequently performed by immersing the separation capillary in a suitable buffer before reaction products can be eluted. Therefore, the technique is limited by the coupling configuration which does not permit the use of different buffer components and/or different pHs during the enzymatic reaction stage and during the separation stage. This limitation is particularly problematic because in most cases the optimum buffer pH for optimum catalytic activity of the immobilized enzyme is completely different from that required for product separation. For example, as applied to protein analysis, trypsin has the greatest catalytic activity at pHs between 8 and 9 while the greatest separation selectivity of peptides occurs over a lower pH range (Wheat et al., *J. Liq. Chromatogr.* 14:987–996, 1991).

Accordingly, there is a need in the art for highly sensitive, fast, and non-labor intensive bioanalytical techniques which are capable of analyzing minute quantities of protein or peptide with a high degree of accuracy. The present invention fulfills these needs, and further provides other related advantages.

SUMMARY OF THE INVENTION

Briefly stated, the present invention provides devices and methods for characterizing proteins and peptides. Within one aspect of the invention, the devices comprise a microenzyme reactor, a separation device, a mass spectrometer and a first interface and a second interface, wherein the first interface is between the microenzyme reactor and the separation device, and the second interface is between the separation device and the mass spectrometer.

Within another aspect of the invention, methods are provided for characterizing a protein or peptide, comprising the steps of: contacting a protein or peptide sample with a microenzyme reactor to provide enzyme products; transferring the enzyme products to a separation device through an interface between the microenzyme reactor and the separation device; resolving the enzyme products into individual components by the separation device; transferring the individual components into a mass spectrometer through an interface between the separation device and the mass spectrometer; and analyzing the individual components by the mass spectrometer, thereby characterizing the protein or peptide.

In one embodiment of the present invention, the microenzyme reactor contains an immobilized enzyme. For example, the microenzyme reactor is a capillary comprised of an inner surface and an outer surface, and an enzyme is immobilized on the inner surface of the capillary. In an alternative embodiment, the microenzyme reactor is a cartridge or a capillary column containing particles, and an enzyme is immobilized on the surface of the particles.

In another embodiment of the present invention, an enzyme(s) contained in the microenzyme reactor adds chemical moiety to a protein or peptide. In an alternative embodiment, an enzyme(s) removes chemical moiety from a protein or peptide.

In another embodiment of the present invention, the interface between the microenzyme reactor and the separation device is a direct attachment via a Teflon sleeve. In an alternative embodiment, the interface between the microenzyme reactor and the separation device is an injection valve.

In yet another embodiment of the present invention, the mass spectrometer is an electrospray ionization mass spectrometer and the interface between the separation device and the mass spectrometer is an electrospray ionization interface.

These and other aspects of the present invention will become evident upon reference to the following detailed description and attached drawings.

DETAILED DESCRIPTION OF THE INVENTION

As noted above, the present invention is directed toward analytical devices and methods for characterizing enzyme modifiable compounds, such as proteins and peptides. Briefly, within one aspect of the present invention, integrated devices are provided comprising (1) a microenzyme reactor for performing various enzymatic reactions, (2) a separation device for separating enzymatic reaction products, and (3) a mass spectrometer for obtaining accurate mass analysis of the individual reaction products. In preferred embodiments of the present invention, the three components are serially coupled to facilitate on-line protein or peptide characterization without excessive sample handling. Through the advantages associated with the combination of these individual components, structural information may be obtained from picogram quantities of protein or peptide.

Within certain embodiments of the invention, the above-noted devices also comprise an interface between the microenzyme reactor and separation device, and an interface between the separation device and the mass spectrometer.

A wide variety of devices may qualify as a "microenzyme reactor" suitable for use within the present invention. Generally, such reactors must be capable of containing the enzyme(s) of interest, as well as the enzyme-modifiable compound. Examples of such enzyme-modifiable compounds include proteins and peptides. As used herein, the terms proteins and peptides represent molecules with two or more amino acids, including polypeptides. Within preferred embodiments of the invention, the enzyme(s) of interest are immobilized onto a solid surface so that a sample contacting the enzyme modified surface is subject to enzymatic action. Suitable surfaces for enzyme immobilization include particles, such as microparticles or microspheres, and the inner surface of a capillary. Accordingly, the microenzyme reactor may take many forms including a cartridge or capillary column loaded with enzyme immobilized microparticles, or a capillary with its inner surface modified with enzyme.

In a preferred embodiment, the microenzyme reactor is constructed by immobilizing specific biochemical enzymes onto the inner surface of a 50 $\mu$m i.d. fused silica capillary (Polymicro Technologies, Phoenix, Ariz.). For capillary columns containing enzyme immobilized microparticles, the microparticles may be made from silica, glass, polystyrene, or other polymeric compositions such as agarose or sepharose®. Suitable capillaries and columns of the present invention have a diameter sufficient to permit efficient flow and yet prevent reduction in their effectiveness through diffusion. The length of the capillary or column of the enzyme reactor is adjustable such that the length is sufficient to contain the amount of immobilized enzyme required for effective enzyme reaction (ie., formation of sufficient quantities of enzyme products in the microenzyme reactor).

Suitable methods for immobilizing enzymes onto solid supports include adsorptive and covalent methods. While adsorptive (ie., non-covalent) methods of enzyme immobilization are simpler in practice than immobilization by covalent techniques, covalently immobilized enzymes are generally preferred because the enzymes remain immobilized longer and are more stable under a wide variety of conditions. Common examples of covalent immobilization include direct covalent attachment of the enzyme to an alkylamine activated support with ligands such as glutaraldehyde, isothiocyanate, and cyanogen bromide.

In a preferred embodiment of the present invention, the enzyme of the microenzyme reactor is immobilized utilizing ligand binding interactions. Briefly, a ligand binding interaction, as used herein, refers to a binding interaction between a ligand and its binding partner. Typically, a ligand is a small molecule and the binding partner is a binding protein or protein fragment. Suitable binding interactions include those interactions between ligands and their binding partners having affinity constants greater than about $10^8$ ($K_a=10^8$, or dissociation constant of $K_d=10^{-8}$). Representative examples of suitable ligand binding pairs include cytostatin/papain, valphosphanate/carboxypeptidase A, biotin/streptavidin, riboflavin/riboflavin binding protein, and antigen/antibody binding pairs. In a particularly preferred embodiment, the enzyme is immobilized utilizing the biotin:avidin ligand binding interaction. Avidin, a binding protein, has a strong affinity ($K_d=10^{-15}$ M) to biotin and is capable of binding four biotin molecules.

Figure 1:
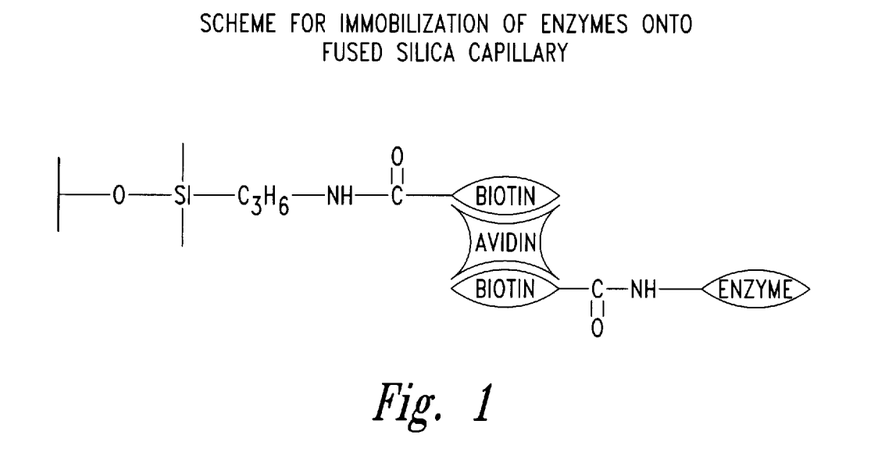
FIG. 1 is a schematic representation of enzyme immobilization through avidin-biotin coupling.
Figure 2:
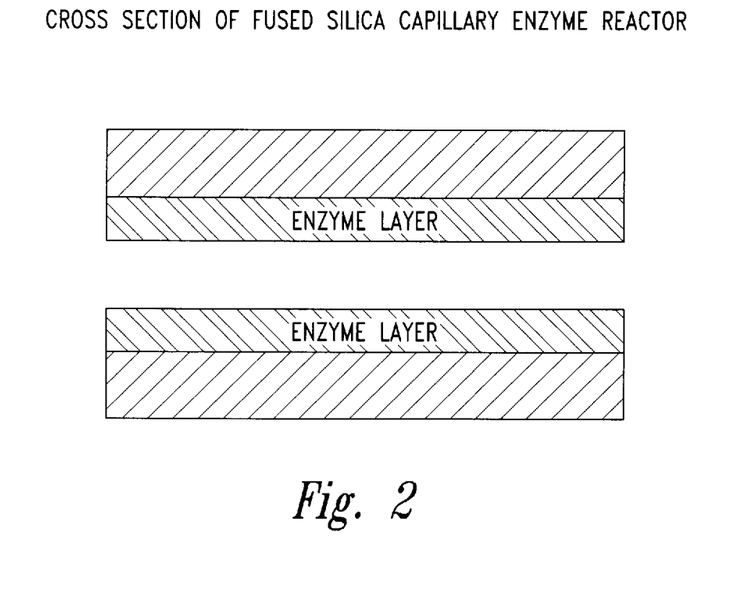
FIG. 2 is a schematic representation of the enzyme modified surface of a microenzyme reactor.

In one embodiment of the present invention, enzymes are immobilized to the inner surface of a capillary by first covalently coupling biotin to the inner surface of a fused silica capillary (the microenzyme reactor) and then treating the biotinylated surface with avidin to provide an avidin immobilized capillary. Finally, the avidin immobilized capillary is treated with a biotinylated enzyme. Thus, the enzyme of the microreactor is immobilized to the inner surface of the silica capillary through a enzyme-biotin:avidin:biotin-surface interaction. The strength of the specific binding between biotin and avidin is sufficiently strong that it can tolerate extreme conditions of temperature, pH and differences in solvent systems. The construction of a representative microenzyme reactor of the present invention is described in detail in Example 1. A schematic representation of enzyme immobilization through avidin-biotin coupling is depicted in FIG. 1, and a schematic representation of a capillary microenzyme reactor is depicted in FIG. 2.

To immobilize an enzyme onto an avidin modified surface, the enzyme must be biotinylated. Briefly, such enzymes may be either chemically biotinylated, or, expressed as a biotinylated protein. Procedures for chemical biotinylation and expression of a representative biotinylated enzyme are presented in Examples 2 and 3, respectively.

Immobilization of enzymes as described above are particularly preferred in the practice of the present invention, since localization of the enzyme away from the capillary surface renders the enzyme more accessible to unhindered interaction with the enzyme-modifiable compound (as enzyme substrate). In a preferred embodiment, each enzyme contains a single biotin located at a position away from the catalytic center of the enzyme. The open tube format of certain reactors described above also offers an additional advantage in that the reactor can be used on-line under low pressure flow conditions. Further, the relatively large surface area-to-volume ratio of the reactor assures adequate interaction between the immobilized enzyme and the substrate to insure complete enzymatic action.

Selection of the enzyme (or enzymes) to be immobilized in the microenzyme reaction will depend upon the nature of the protein (or peptide) characterization or analysis to be performed. Briefly, because of the versatile nature of the enzyme immobilization technique of the present invention, many different types of enzymes may be readily immobilized in the microenzyme reactor. As a result, a wide variety of reaction products may be derived from treating a protein (or peptide) to one or more microenzyme reactors. Accordingly, analysis and identification of these enzyme products (modified proteins and peptides) by subsequent separation and identification provides a set of information unique for each protein (or peptide) and useful in either identifying the protein, probing the primary structure of the protein (or peptide), or evaluating the protein's (or peptide's) reactivity toward the particular immobilized enzyme. The evaluation of a protein's or peptide's reactivity toward an immobilized enzyme provides information related to the enzyme's capacity and specificity toward the protein or peptide as substrate and may also be useful in screening proteins and peptides for enzyme activity.

In one embodiment of the present invention, the enzymes immobilized onto the microenzyme reactor include enzymes which digest proteins or peptides. Such enzymes may be broadly referred to as peptidases, and include enzymes such as various aminopeptidases, carboxypeptidases, and endopeptidases (e.g., trypsin). Amino and carboxypeptidases are useful in characterizing post-translational modifications and processing events.

In another embodiment of the present invention, the immobilized enzymes are enzymes which modify proteins or peptides by adding various groups to the protein or polypeptide. Such modifying enzymes include glycosylating enzymes that add sugar moieties (i.e., sugar-modifying enzymes such as galactosyltransferase, fucosyltransferase, sialyltransferase, and mannosyltransferase) and phosphorylating enzymes that add phosphate groups (i.e., various protein kinases).

Alternatively, in a further embodiment of the present invention, the immobilized enzymes include enzymes which modify the protein or peptide by the removal of post-translational protein modifications. Such modifying enzymes include enzymes which remove sugar moieties from glycoproteins (i.e., sugar-modifying enzymes such as glycosidases, galactosidase, fucosidase, sialidase, and mannosidase) and phosphate groups from phosphoproteins (i.e., various phosphatases).

The following describes representatives of enzymes and their functions as immobilized enzymes that may be used in the practice of the present invention.

Briefly, glycosylation is a common post-translational modification of proteins or peptides which involves the introduction of monosaccharides, oligosaccharides and polysaccharides as a covalent component. Glycosylation affects protein activity in numerous ways, including protein folding, transport, in vivo dissolution, physical stability, protease resistance and specific bioactivity. Glycosylation is catalyzed in vivo by various glycosyltransferases which are present in large quantities in the endoplasmic recticulum (ER) and the Golgi apparatus. Although most glycosylated proteins locate extracellularly, there is evidence to suggest that O-glycosylation of serine residues with N-acetylglucosamine does occur in a number of intracellular proteins including nuclear pore proteins.

Glycosylation of proteins or peptides may occur in at least three different ways. Carbohydrate attachment as side chains of the polypeptide chain occurs via either an N- or O-glycosidic linkage to either asparagine (N-linkage) or serine and threonine (O-linkage) residues. Also, modification at the carboxy terminal occurs via a glycosylphosphatidyliniositol (GPI) linkage which functions to anchor the protein to the membrane. Protein side chain modification with carbohydrates is very specific and occurs according to specific amino acid sequence motif surrounding the modified amino acid residue. Only a few amino acid residues are susceptible to glycosylation. For example, characterization of glycosylated asparagine residues in a variety of glycoproteins reveals a required tripeptide sequence, Asn-X-Ser (Thr), for glycosylation to occur. X can be any amino acid, except proline or aspartic acid.

In general, glycosylated proteins contain very complex carbohydrate structures. Protein glycosylation is a dynamic process and is reversible in vitro via enzymatic catalysis. Only limited evidence of in vivo deglycosylation has been reported to date. In practice, the determination of the site of attachment and the structure of the attached carbohydrate involves sequential de-glycosylation using different specific glycosidases.

A wide variety of enzymes may be used to assess glycosylation of proteins and peptides. Representative examples of enzymes which add glycosyl groups ("Modifying Enzymes") include N-acetylglucosaminyltransferase, galactosyltransferases, fucosyltransferase, sialyltransferase and mannosyltransferase. Representative examples of enzymes which remove glycosyl groups include glycosidases (endo and exo), galactosidase, fucosidase, sialidase, and mannosidase.

Other post-translational modifications such as phosphorylation may also be determined with the devices and methods disclosed herein. Briefly, phosphorylation is a dynamic post-translational modification of proteins and peptides involving the covalent attachment of phosphate groups to specific amino acid residues in the protein or peptide chain. Protein phosphorylation is at present widely recognized as a major mechanism for information relay and processing within the microcosm of the eukaryotic cell. Phosphate attachment to amino acid residues in the protein or peptide chain can be classified into three groups; O-phosphates, N-phosphates, and acyl-phosphates. In terms of quantity and extent of distribution, attachment via O-phosphate linkage is by far the main mode of modification of proteins with phosphate groups. Phosphorylation in general is very specific and is limited to only very few amino acid residues in a protein. The O-phosphate linkage is specific to only the amino acid residues serine, threonine, and tyrosine, while modification via the N-phosphate linkage is limited to basic amino acid residues such as arginine, histidine, and lysine.

Phosphorylation is reversible both in vivo and in vitro. Phosphorylation is an enzymatically mediated process, and is catalyzed by several different classes of kinases. These enzymes catalyze the transfer of the gamma-phosphate of the nucleotide triphosphate to specific amino acid residues of the substrate polypeptide to give a phosphomonoester. Although it is very difficult to ascertain the specificity of protein kinases, the specific recognition sequence for some protein kinases have been determined. For other protein kinases, it appears that various acidic and basic residues within a particular location relative to the modified residue are sufficient to define a recognition motif. As noted above, protein phosphorylation is easily reversed both in vivo and in vitro. Dephosphorylation of phosphorylated proteins is catalyzed by protein phosphatases. Listed below are some general classes of enzymes that have been found catalyze either the phosphorylation or dephosphorylation of proteins.

| Modifying Enzymes | Demodifying Enzymes |
| --- | --- |
| Protein-serine-threonine kinases | Protein-Phosphatases |
| Cyclic AMP-dependent protein kinases (I, II) | Serine/threonine-phosphatases (Types 1 and 2) |
| Cyclic GMP-dependent protein kinases | Serine/threonine-phosphatases (Types 1 and 2) |
| Calcium-dependent protein kinases | Serine/threonine-phosphatases (Types 1 and 2) |
| Double-stranded RNA-dependent protein kinase | Serine/threonine-phosphatases (Types 1 and 2) |
| Protein-tyrosine kinases | Protein-tyrosine phosphatases |

The most common post-translational modifications of proteins involve the covalent attachment of various different chemical moieties to either the carboxyl group of the carboxy-terminal amino acid residue, or the amino group of the amino-terminal amino acid residue. All of these modifications have been found to play a significant role in either the bioactivity or the stability of the protein. The most common modification of the α-carboxyl group of the C-terminal amino acid residue involves the conversion of the carboxyl group to an amide group via an amide linkage. This modification is catalyzed in vivo by the enzyme peptidyl-glycine-α-amidating monooxygenase (PAP). This enzyme is very strict in specificity and is mostly active towards peptides with a carboxy-terminal glycine residue.

The most common modification of the amino-terminal amino acid residue involves the attachment of various chemical groups via the N-acyl linkage to the α-amino group of this residue. Some of the common modifying groups found to date include: formyl, acetyl, pyruvoyl, myrislyl, glucuronyl, an amino acyl, pyroglutamate, and murine. N-α-acetylation is by far the most common modification found in proteins from different sources. This post-translational modification is catalyzed by the enzyme acetyl transferase and involves the transfer of acetyl group from the enzyme to the protein.

Covalent attachment of long fatty acids to proteins is also a common post-translational modification. Fatty acids are attached via an acyl linkage and occurs in three distinct ways: (1) attachment by a thioester or an ester bond to cysteine, serine or threonine residues; (2) attachment by an amide linkage to the amino group of the N-terminal residue; (3) attachment by the carboxyl linkage to the C-terminal amino acid residue. Protein modification by fatty acids is also mediated by enzymes. These enzymes are very specific in terms of activity towards different amino acids, as well as location of the modified residue. Although reversibility of some of these modifications has been demonstrated in vitro, evidence for reversibility invivo is very scarce. Listed below are some enzymes that have been found to be active towards the release of some of these modifying groups from proteins.

| Enzyme | Specificity |
| --- | --- |
| Aminopeptidases | N-terminal amino acid residues |
| Acylamino Acid releasing enzymes | Acylated amino-terminal amino acids |
| Carboxypeptidases(C,Y) | Amino acid residues at the carboxy terminal of proteins |
| PCA'se | Amino-terminal pyroglutamate |
| Demyristylating enzymes | Amino-terminal myrislate |

As mentioned above, in one embodiment of the present invention, devices are provided for the characterization of proteins and peptides comprise (1) a microenzyme reactor, (2) a separation device, (3) an interface between the microenzyme reactor and the separation device, (4) a mass spectrometer, and (5) an interface between the separation device and the mass spectrometer. Alternatively, as mentioned above, more than a single microenzyme reactor may be employed to generate enzyme products. The use of two or more microenzyme reactors thus produces additional characterization information. In the practice of the present invention, two or more microenzyme reactors may be arranged either in series or in parallel. For example, in a series arrangement of two microenzyme reactors, the reaction products of the first microenzyme reactor are eluted into a second microenzyme reactor prior to being directed to the separation device for component resolution and ultimately to the mass spectrometer for identification. In a parallel arrangement of two or more microenzyme reactors, a single sample of enzyme-modifiable compounds may be introduced into two or more parallel microenzyme reactors and the reaction products of each microenzyme reactor may then be sequentially eluted into the separation device, and ultimately identified by mass spectrometry.

In the practice of the present invention, the coupling of the microenzyme reactor to the separation device is achieved by an interface between the microenzyme reactor and the separation device. Where both the microenzyme reactor and the separation device are capillaries, the two may be joined together within a sleeve made from Teflon tubing. Where the enzyme reactor is a capillary column, the interface between the microenzyme reactor and the separation device is an injection valve. Suitable injection values include standard liquid chromatographic injection values. In a preferred embodiment, the injection value is a Rheodyne 8125 value containing a 20 μl injection loop.

The enzyme products produced by the microenzyme reactor travel from the reactor via the interface to the separation device. The separation device resolves the enzyme products into their individual components. Suitable separation devices include liquid chromatographic columns and capillary electrophoretic capillaries. Preferred liquid chromatographic columns include micro high performance liquid chromatographic columns, for example, reverse-phase, ion-exchange, and affinity columns. In a preferred embodiment, the separation capillary is a capillary electrophoretic capillary.

The resolution of the enzyme products into their individual polypeptide components by the separation device allows for the sequential introduction of the individual reaction products into the mass spectrometer for identification of the individual product components. The coupling of the separation device to the mass spectrometer is accomplished through an interface. For capillary electrophoretic separation devices, the interface between the separation device and the mass spectrometer is as generally described by Thibault et al. (*J. Chromatogr.* 542:483–501, 1991).

For operation on-line with a CE instrument, the original ionspray interface setup was modified according to an earlier design in order to provide both a coaxial liquid sheath as well as a coaxial gas sheath (Thibault et al., ibid., 1991). The double coaxial interface consisted of two tees (Valco) and a stainless steel needle. The back tee was used to provide the liquid sheath make-up solution necessary for good electrical conductivity for the CE separation and also for the maintenance of good electrospray. The liquid sheath was supplied by a 50 μm i.d., 150 mm o.d. fused silica capillary at a flow rate of 6.0 μl/min. and was pumped from a reservoir by a liquid chromatography pump (Shimadzu, LC-10AD, Shimadzu Corp., Kyoto, Japan) via a valve (Rheodyne, No. 8125). This sheath liquid was composed of 0.2% formic acid in 50% methanol/water. The front tee was used for introduction of the nebulization sheath gas and to connect the high voltage cable for the ion spray needle. The nebulization sheath gas was supplied via 1 mm i.d. Teflon tubing at a rate of 2L/min. The CE capillary protruded about 0.1 mm from the ionspray needle which in turn protruded about 0.5 mm from the concentric nebulizer sheath gas needle. A drying nitrogen curtain gas at ambient temperature was supplied at a flow rate of 1.8 L/min. to the region between the ionspray ionization source and the mass spectrometer orifice.

In the present invention, the identification of the enzyme reaction products is achieved by a mass spectrometer (See generally Burlingame et al., *Anal. Chem.* 64:467R–502R, 1992). Various mass spectrometers may be used within the present invention. Representative examples include: triple quadrupole mass spectrometers, magnetic sector instruments (magnetic tandem mass spectrometer, JEOL, Peabody, Mass), ionspray mass spectrometers (Bruins et al., *Anal Chem.* 59:2642–2647, 1987), electrospray mass spectrometers (Fenn et al., *Science* 246:64–71, 1989), laser desorption time-of-flight mass spectrometers (Karas and Hillenkamp, *Anal. Chem.* 60:2299–2301, 1988), and a Fourier Transform Ion Cyclotron Resonance Mass Spectrometer (Extrel Corp., Pittsburgh, Mass.). Within a particularly preferred embodiment, a triple quadrupole mass spectrometer with an electrospray or ionspray ionization source (model API III, Sciex, Thornhill, Ontario, Canada) is utilized to ionize the derivatized terminal amino acid, and to determine its molecular weight.

In a preferred embodiment, the mass spectrometer is an electrospray ionization mass spectrometry (ESI/MS). In essence, the mass spectrometer is the detector for the analytical device of the present invention. Electrospray ionization mass spectrometry provides an accurate and sensitive means of obtaining mass analysis of polypeptide samples. Moreover, ESIIMS is compatible with on-line liquid flow systems and has the sensitivity and speed for the analysis of complex proteins and their mixtures. The accuracy of mass measurement with ESI/MS is on the order of 1–2 Da throughout the mass range 100,000 Da and the capability of electrospray ionization to create multiply charged ions during the ionization process significantly extends the mass range of proteins that can be analyzed by the technique. Consequently, ESI/MS offers a means of rapidly characterizing post-translational modifications of natural and recombinant proteins and peptides.

Figure 4:
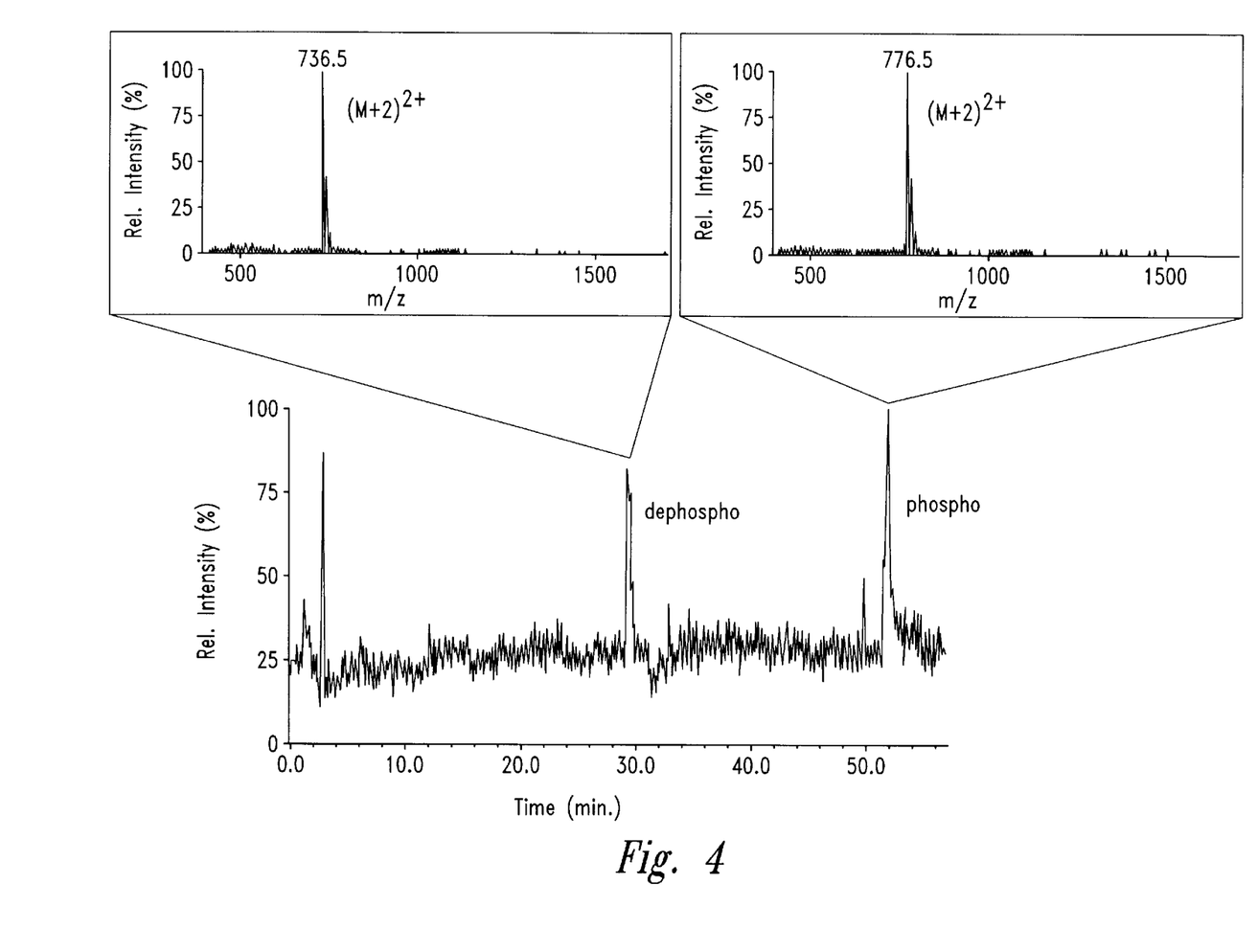
FIG. 4 illustrates mass spectral data for the enzymatic dephosphorylation of a phosphorylated peptide corresponding to the region between amino acids 851–864 of the platelet derived growth factor receptor (peptide PDGFR) obtained by the ER/CE/ESIMS of the present invention.

A representative schematic of the analytical device of the present invention is shown in FIG. 4 and described in detail in Example 4. With this design a complete peptide map including the identification of type and site of post-translational amino acid modification can be obtained on as little as picogram amounts of starting protein.

In another aspect of the present invention, a method for characterizing sub-nanogram quantities of proteins and peptides is disclosed. The method includes the steps of (1) introducing the protein or peptide sample to be characterized into the microenzyme reactor and incubating the sample in the reactor for a predetermined time for the specific enzymatic reaction to occur, thereby producing enzyme products; (2) transferring the entire enzyme reaction products directly to the separation device, through an interface between the microenzyme reactor and separation device, to resolve the enzyme products into their individual components; and (3) sequentially eluting the individual components into the mass spectrometer, through an interface between the separation device and the mass spectrometer, for mass analysis. The method of the present invention is also suited for integration with conventional peptide mapping techniques involving gel separated proteins, thus eliminating the problem of obtaining intact polypeptides in a reliable form which is normally the limitation of manipulating small amounts of proteins.

In the practice of the present invention, protein and peptides are characterized based on mass analysis of their products resulting from contact with the enzyme or enzymes of a microreactor. The sample protein or peptide is incubated in the microenzyme reactor for a period of time and results in the production of enzyme products. The enzyme products, which will depend upon the nature of the protein or peptide introduced into the microenzyme reactor and the enzyme(s) present, are then resolved into their component peptides by the separation device and subsequently eluted into the mass spectrometer for mass analysis.

The method of the present invention is a comparative method, i.e., the results of one analysis (introducing a protein sample into the enzyme microreactor, resolving the enzyme products into their individual components, and eluting the component into the mass spectrometer for mass analysis) are compared to the results of another analysis utilizing the same protein or peptide sample. In the practice of the invention, a protein sample is introduced into a device of the present invention, and the incubation of the sample in the microenzyme reactor is limited to such a time as to permit only partial enzymatic reaction (i.e., the protein or peptide sample is not completely digested or modified). In a second analysis, the incubation time is varied and therefore the quantitative aspects of the enzyme reaction products are changed (i.e., for longer incubation times within the reactor, more enzyme product is formed and less starting protein remains). The mass analysis comparison permits the observation of the mass shift between the enzyme product and the starting protein or peptide. The mass analysis thus permits the identification of the modification. For example, where the enzyme reactor bears a dephosphorylating enzyme, on short reaction times a phosphorylated protein will produce a mass analysis that reveals the starting phosphorylated protein and perhaps some dephosphorylated enzyme product. At longer incubation times, the mass analysis will show dephosphorylated enzyme product and perhaps some starting phosphorylated protein. Comparison of the mass analyses for the two runs will identify the starting material and enzyme products as related by their mass shift, a shift corresponding to the loss of phosphate group from the phosphorylated protein sample.

The representative performance of the on-line microcharacterization system of the present invention in the dephosphorylation of the peptide phosphoPDGFR and the tryptic digest of peptide PDGFR are presented in Examples 5 and 6, respectively.

The following examples are offered by way of illustration, and not by way of limitation.

EXAMPLES

CHEMICALS and REAGENTS: Water was distilled and deionized (Millipore, Bedford, Mass.). Sodium bicarbonate, ammonium bicarbonate, sodium phosphate (monobasic and dibasic), acetone, were obtained from Fisher Scientific (Fairlawn, N.J.). ExtrAvidin and ammonium formate were obtained from Sigma (St. Louis, Mo.). NHS-LC-biotin (Sulfosucciniimidyl 6-(biotinamido)hexanoate) was obtained from Pierce (Rockford, Ill.). (3-aminopropyl) triethoxysilane, (3-APTS) was obtained from Aldrich Chemical Co., Inc., Milwaukee, Wis. All synthetic test phosphopeptides were synthesized at the Biomedical Research Centre, University of British Columbia, Vancouver, Canada. All reagents were used as received without further purification.

SUPPLIES and EQUIPMENT: Fused silica capillary was purchased from Polymicro Technologies, Phoenix, Ariz. Appropriate lengths of the capillary were used for either making the enzyme-modified reactor or as the separation capillary. Capillary electrophoresis separation was performed on the Quanta 4000, Waters Corporation, Boston, Mass. Mass spectrometric analysis was performed on a prototype of a single Quad mass spectrometer with an attached electrospray ionization interface. Sciex, Thornhill, ONT, Canada.

Example 1

Representative Construction of a Microenzyme Reactor

The microenzyme reactor was constructed essentially as described in Amankwa and Kuhr, *Anal. Chem.* 64:1610–13, 1992. Briefly, the inner surface of a fused silica capillary is first modified with 3-aminopropyltriethoxysilane (3-APTS) which provides free amino groups on the capillary surface to which biotin can be coupled through the formation of an amide bond. The reaction was performed by slow perfusion of the capillary with 5 mg/ml of NHS-LC-biotin in aqueous sodium (pH 8.6). Subsequent treatment (overnight) at 4° C. of the biotin modified surface bicarbonate with ExtrAvidin 10 mg/ml in sodium phosphate (pH 7.2) yields an avidin modified capillary. The final step in the microenzyme reactor construction involves the perfusion of the avidin modified capillary with the crude biotinylated HPTP-B cell lysate overnight at 4° C.

Example 2

Chemical Biotinylation of Proteins

Chemical modification of proteins with biotin is routinely performed under controlled conditions as described in the Pierce Handbook (Pierce, Rockford, Ill.). Typically, two molar equivalents of biotin is added to a solution of the protein to be biotinylated in about 50 mM sodium bicarbonate, pH 8.5. After incubating on ice for about two hours, unreacted biotin is removed by centrifugation using either an appropriate Centricon-Microconcentrator, size exclusion chromatography, or dialysis.

Example 3

Procedure for Expression of Biotinylated Fusion Protein

Materials The plasmid pHPTP-B was cloned as described by Harder et al. (*Biochem. J.* 298:395–401, 1994) and all the necessary reagents required for recombinant protein expression and cell lysis were acquired from commercial sources (Stratagene, LaJolla, Calif.). PinPoint Xa-2™ Vector and accessories (cat. #V4201) were purchased from Promega Corporation, Madison, Wis.

Buffers for protein isolation and purification

Buffer A: 25 mM Tris-HCl pH 7.5, 50 mM NaCl, 5 mM 2-mercaptoethanol. Buffer B: same as buffer A except that it also contains soybean trypsin inhibitor (0.6 $\mu$g/ml), leupeptin (0.5 $\mu$g/ml), phenylmethylsulfonylfluoride (1 mg/ml), and pepstatin (0.7 $\mu$g/ml).

Expression of in vivo biotinylated HPTP-B

The expression of the biotinylated HPTP-B was performed as previously described for the expression of pET-HPTPB (Harder et al., *Biochem J.* 298:395–401, 1994). Briefly, plasmid pHPTP-B was digested with HindIII and Bgl II and the cDNA fragment was then subcloned into HindIII and Bgl II digested PinPoint Xa-2™ plasmid, to give PinPoint-HPTP-B. This plasmid was then transformed into Competent XL1-Blue *E. coli* strain bacteria (Stratagene, LaJolla, Calif.). This strain contains an integrated copy of the T7 RNA polymerase gene and is under the control of the isopropyl thiogalactoside (IPTG) inducible lac Uv5 promoter. A 20 ml overnight culture of PinPoint-HPTP-B grown in 100 $\mu$g/ml ampicillin/Luria broth was added to 1 liter of the same media and grown with shaking to O.D. 0.7 at 37° C. in the absence of IPTG. Recombinant fusion protein production was simulated by the addition of 1 mM IPTG. After 4–5 hours of induced growth the bacteria cells were pelleted by centrifugation at 3,500 rpm for 15 min. at 4° C. (Beckman J-6B). The cells (2 ml) were then washed in buffer A, sedimented and then resuspended in 5 ml of buffer B. 770 $\mu$l of 10 mg/ml lysozyme was added and the mixture incubated on ice for 15 min. Three cycles of alternating freeze-thaws in liquid nitrogen were performed to ensure cell lysis. Later, 55 $\mu$l of 1M $MgCl_2$ and 50 $\mu$l of 10 mg/ml DNase 1 were added to the lysate. The resulting mixture was incubated at 25° C. for 20 min., 100 $\mu$l of 500 mM EDTA and 600 $\mu$l of 10% Triton X-100 were then added, mixed and reincubated for a further 30 min. at 25° C. Finally, the lysate was subjected to Ultra-centrifugation at 19,000 rpm at 4° C. for one hour. The supernatant was carefully separated, frozen in liquid nitrogen and stored at –80° C. until ready for use.

Example 4

Figure 3:
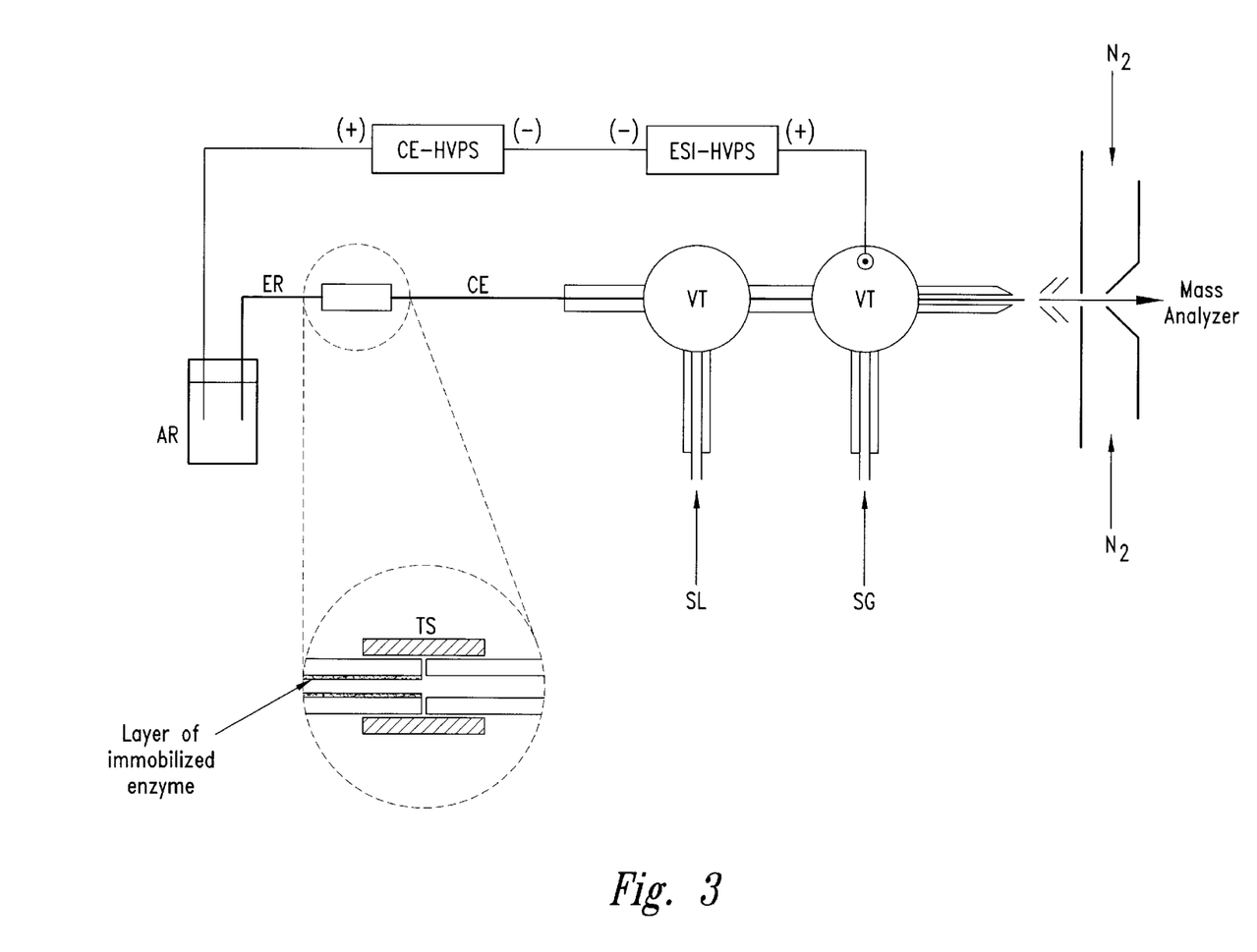
FIG. 3 is a schematic diagram showing the instrumental design of a microenzyme reactor/capillary electrophoresis/ electrospray ionization mass spectrometer (ER/CE/ESIMS) of the present invention.

Representative Performance of the On-Line Microcharacterization System: Dephosphorylation of PhosphoPDGFR A schematic diagram of a protein or peptide characterization device of the present invention, the on-line microenzyme reactor/capillary electrophoresis/mass spectrometer (ER/CE/MS), is shown in FIG. 3. The following abbreviations are used in the figure: ER, enzyme reactor consisting of 2.5 cm of HPTP-$\beta$ modified fused silica capillary; CE, capillary; TS, Teflon sleeve; AR, anode reservoir; CE-HVPS, capillary electrophoresis high voltage power supply; ESI-HVPS, electrospray ionization high voltage power supply; VT, valco tee; SL; sheath liquid; SG, sheath gas; $N_2$, nitrogen gas. Details of the interface between the enzyme reactor and the CE separation capillary are shown in the insert.

The performance of this device is demonstrated by the dephosphorylation of peptide phosphoPDGFR. PDGFR is a synthetic phosphopeptide which corresponds to one of the phosphorylation sites on the human PDGF receptor B-chain and contains one phosphorylated tyrosine at position 857 from the amino terminus. In this example, phosphoPDGFR is subjected to reaction with biotinylated HPTP-B (prepared as described above in Example 3) immobilized onto the microenzyme reactor (constructed as described above in Example 1). After incubation in the microenzyme reaction, the enzyme products were transferred to the separation capillary and resolved into their individual components which were subsequently eluted into the electrospray ionization mass spectrometer.

An aliquot of sample containing 3 pmol of phospho PDGFR was injected onto an HPTP-$\beta$ microenzyme reactor. After incubation in the reactor for 6.5 minutes, the enzyme reaction products were transferred to the separation capillary for resolution and subsequently eluted and analyzed by the electrospray ionization mass spectrometer. Mass spectra data for the on-line ER/CE/MS dephosphorylation of the test synthetic phosphopeptide is shown in FIG. 4, which shows the total ion current (TIC) corresponding to the electropherogram for m/z=500–1700. In the figure, the peak corresponding to the substrate, phosphopeptide, is labeled "phospho," while the peak corresponding to the product, dephosphorylated peptide is labeled "dephospho." The mass spectra for these peaks are shown as inserts. Other experimental conditions included: the enzyme reactor (ER) was 2.5 cm of HPTP-$\beta$ modified fused silica capillary; the separation capillary (CE) was 138 cm long; 3 pmol of phosphorylated PDGFR-857 was injected electrokinetically (20 s at 25KV) into the microenzyme reactor and allowed to incubate there for 6.5 min before initiation of CE separation.

Unambiguous identification by mass of both the substrate and product are easily made. The peak designated "phospho" corresponds to the residual of the original phosphopeptide while, the peak designated "dephospho" corresponds to the dephosphorylated reactor produced from the original phosphopeptide. The mass spectra of these peaks are also shown as inserts respectively. The apparent mass difference of 40 Da (776.5–736.5) corresponds to a net mass difference of 80 Da between the $[M+H]^+$ ions of these species which is indicative of a loss of a phosphate ($HPO_3$) group. Also, comparison of the ion currents for the phospho and dephospho forms show that about 50% (1.5 pmol) of the original phosphopeptide injected onto the enzyme reactor was dephosphorylated within the 6.5 min incubation time by the enzyme reactor.

Example 5

Figure 5A:
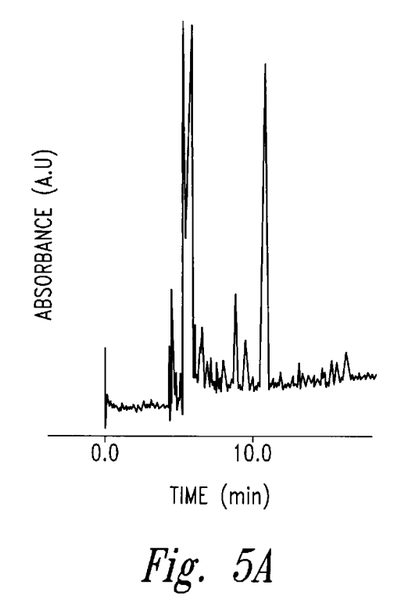
FIG. 5 illustrates CE electropherogramns obtained by ER/CE analysis of a 51 final tryptic digest of phosphorylated PDGFR. Panel A shows the CE electropherogram of the sample. Panel B shows the electropherogramn obtained after on-line ER/CE was performed.
Figure 5B:
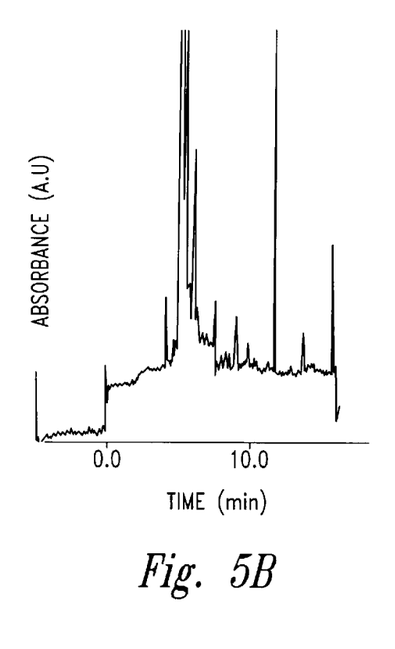

Representative Performance of the On-Line Microcharacterization System: Tryptic Digest of PDGFR The capability of this technique was also demonstrated by applying it to the identification of the phosphorylated peptide in a mixture. A tryptic digest of phosphopeptide PDGFR containing three smaller fragments IMR, DSNYpISK, and GST designated T1, T2 and T3 respectively was obtained by exhaustively digesting it with trypsin immobilized on DITC glass (Sigma, St. Louis, Mo.). An aliquot (51 fmol) of this digest was analyzed by CE with on-column UV absorbance detection and then by an on-line ER/CE. The electropherograms for these analyses are shown in FIGS. 5A and 5B, respectively. In the figures, A refers to the CE electropherogram of the sample and B refers to the electropherogram obtained after on-line ER/CE was performed. The experimental conditions included: the enzyme reactor (ER) was 2.5 cm of HPTP-β modified fused silica capillary; samples were injected for 2 s by vacuum suction (15 inches of Hg); and during on-line ER/CE, the sample was allowed to incubate in the enzyme reactor for 6.5 min before initiation of CE separation (time=0.0 min).

Figure 6:
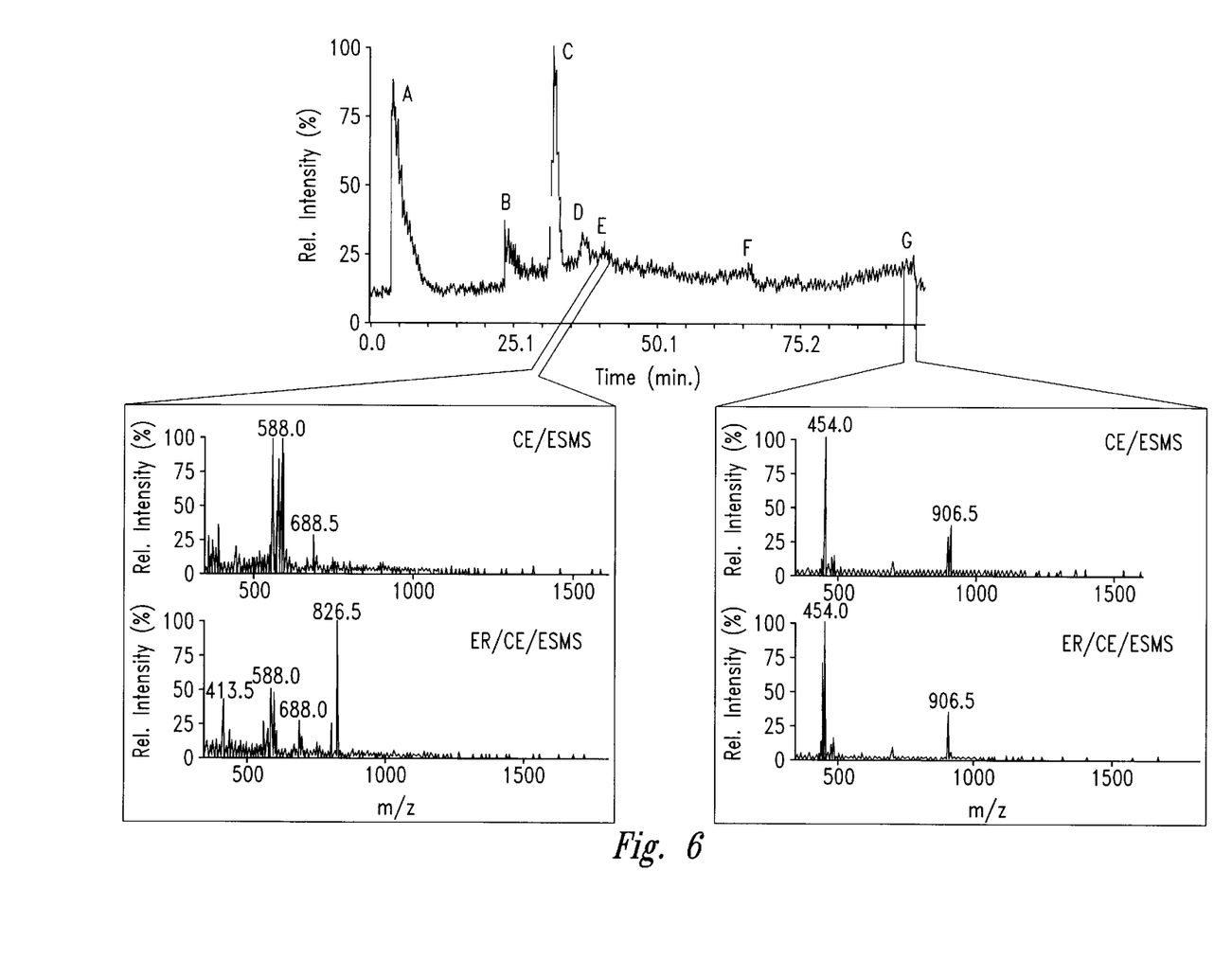
FIG. 6 illustrates mass spectral data for the tryptic digest of phosphorylated PDGFR obtained by an ER/CE/ESIMS of the present invention.

Comparison of FIGS. 5A and 5B shows a distinct difference between the two electropherograms. The peak at Retention Time (RT)=10 min in FIG. 5A is absent in FIG. 5B while a new peak (RT=7.5) is present in FIG. 5B. (Note: the slight difference between the elution times of the peaks in FIGS. 5A and 5B was the result of the smaller electroomotic flow caused by the coupling of the enzyme reactor to the CE separation capillary). The peak with RT=10 was due to the phosphorylated peptide fragment in the tryptic mixture while the new peak in FIG. 5B was due to the dephospho form of that peptide. To confirm the result in FIG. 5, the experiment was repeated, except that this time the eluting peaks were subjected to mass analysis with the on-line electrospray mass spectrometer. A larger amount (13.9 pmol) of the digest was also used. The results are shown in FIG. 6. The figure presents mass spectral data showing the TIC electropherogram obtained for on-line ER/CE/ESIMS of 13.9 pmol of tryptic digest of phosphorylated peptide PDGFR utilizing an enzyme reactor, 2.5 cm of HPTP-β modified fused silica capillary. The sample was incubated on the enzyme reactor for 6.5 min before initiation of CE separation. The inserts are the mass spectra of the scans under peaks E and G. Inserts indicate; mass spectra of the scans in the region corresponding to peak E when only on-line CE/ESIMS was performed (TIC electropherogram not shown); mass spectra of the scans in the region corresponding to peak E when on-line ER/CE/ESIMS was performed; and mass spectra of the scans in the region corresponding to Peak G.

The longer elution times in FIG. 6 compared to those in FIG. 5 is due to the fact that about twice as long separation capillary was used in the on-line ER/CE/MS mode. The extra length was necessary in order to connect the separation capillary to the electrospray ionization interface on the mass spectrometer. Mass spectra of all the peaks E and G are shown as inserts. The mass spectra of peak G in both runs (CE/MS and ER/CE/MS) indicate masses at m/z=454.0 and m/z=906.5 (see inserts). Complete dephosphorylation was not achieved because a large amount (13.9 pmol) of substrate was injected onto the enzyme reactor. These masses correspond respectively to the $[M+2H]^{2+}$ and $[M+H]^+$ ions of the tryptic fragment T2. The spectra under peak E is, however, different for the two experiments. The mass spectra under peak E in the electropherogram of the ER/CE/MS experiment shows distinctly signals at m/z=826.5 and m/z=413.5 (see insert ER/CE/MS). These signals are clearly absent in the spectra under peak E in the electropherogram obtained when only CE/MS was performed (see insert CE/ESMS). The loss of a phosphate group ($HPO_3$) from the tryptic fragment T2 (DSNYpISK) yields a peptide, DSNYISK, with an $[M+H]^+$ ion mass of 826.5 which is exactly the mass signal found under Peak E when ER/CE/MS was performed. Consequently, Peak E in FIG. 6 is due to the product of the dephosphorylation of tryptic fragment T2 caused by the enzyme reactor. Tryptic fragment T2 was consequently identified as the one containing the phosphorylated amino acid residue. Because the enzyme immobilized in the reactor is only active against phosphotyrosine and since fragment T2 contains only one tyrosine residue, the amino acid residue at position 857 is therefore the site of phosphorylation.

From the foregoing, it will be evident that, although specific embodiments of the invention have been described herein for purposes of illustration, various modifications may be made without deviating from the spirit and scope of the invention.

We claim:

1. A device for the characterization of proteins and peptides comprising an enzyme reactor, a separation device, a mass spectrometer and a first interface and a second interface, said first interface between the enzyme reactor and the separation device and said second interface between the separation device and the mass spectrometer.

2. A device according to claim 1 wherein said enzyme reactor contains an immobilized enzyme.

3. A device according to claim 2 wherein said enzyme reactor is a capillary comprised of an inner surface and an outer surface, and wherein said enzyme is immobilized on the inner surface of said capillary.

4. A device according to claim 2 wherein said enzyme reactor is a cartridge or a capillary column containing particles, and wherein said enzyme is immobilized on the surface of said particles.

5. A device according to claim 2 wherein said enzyme is immobilized by covalent coupling.

6. A device according to claim 2 wherein said enzyme is immobilized by ligand binding interactions.

7. A device according to claim 2 wherein said enzyme is immobilized by avidin-biotin coupling.

8. A device according to claim 2 wherein said enzyme is biotinylated.

9. A device according to claim 2 wherein said enzyme adds a chemical moiety to a protein or peptide.

10. A device according to claim 2 wherein said enzyme removes a chemical moiety from a protein or peptide.

11. A device according to claim 2 wherein said enzyme is a transferase.

12. A device according to claim 2 wherein said enzyme is a kinase.

13. A device according to claim 2 wherein said enzyme is a phosphatase.

14. A device according to claim 2 wherein said enzyme is a sugar modifying enzyme.

15. A device according to claim 1 wherein said separation device is an electrophoretic capillary.

16. A device according to claim 1 wherein said separation device is a liquid chromatographic column.

17. A device according to claim 16 wherein said liquid chromatographic column is a reverse-phase column.

18. A device according to claim 1 wherein said first interface is a direct attachment via a Teflon sleeve.

19. A device according to claim 1 wherein said first interface is an injection valve.

20. A device according to claim 1 wherein the mass spectrometer is an electrospray ionization mass spectrometer.

21. The device of claim 20 wherein said second interface is an electrospray ionization interface.

22. A method for characterizing a protein or peptide, comprising the steps of:
(a) contacting a protein or peptide sample with an enzyme reactor to provide enzyme products;
(b) transferring said enzyme products to a separation device through an interface between the enzyme reactor and the separation device;
(c) resolving said enzyme products into individual components by said separation device,
(d) transferring said individual components into a mass spectrometer through an interface between the separation device and the mass spectrometer; and
(e) analyzing said individual components by said mass spectrometer, thereby characterizing said protein or peptide.

23. A method according to claim 22 wherein said enzyme reactor contains an immobilized enzyme.

24. A method according to claim 22 wherein said enzyme reactor is a capillary comprised of an inner surface and an outer surface, and wherein said enzyme is immobilized on the inner surface of said capillary.

25. A method according to claim 22 wherein said enzyme reactor is a cartridge or a capillary column containing particles, and wherein said enzyme is immobilized on the surface of said particles.

26. A method according to claim 23 wherein said enzyme is immobilized by covalent coupling.

27. A method according to claim 23 wherein said enzyme is immobilized by ligand binding interactions.

28. A method according to claim 23 wherein said enzyme is immobilized by avidin-biotin coupling.

29. A method according to claim 23 wherein said enzyme is biotinylated.

30. A method according to claim 23 wherein said enzyme adds a chemical moiety to the protein or peptide.

31. A method according to claim 23 wherein said enzyme removes a chemical moiety from the protein or peptide.

32. A method according to claim 23 wherein said enzyme is a transferase.

33. A method according to claim 23 wherein said enzyme is a kinase.

34. A method according to claim 23 wherein said enzyme is a phosphatase.

35. A method according to claim 23 wherein said enzyme is a sugar modifying enzyme.

36. A method according to claim 22 wherein said separation device is an electrophoretic capillary.

37. A method according to claim 22 wherein said separation device is a liquid chromatographic column.

38. A method according to claim 37 wherein said liquid chromatographic column is a reverse-phase column.

39. A method according to claim 22 wherein said interface between the enzyme reactor and the separation device is a direct attachment via a Teflon sleeve.

40. A method according to claim 22 wherein said interface between the enzyme reactor and the separation device is an injection valve.

41. A method according to claim 22 wherein said mass spectrometer is an electrospray ionization mass spectrometer.

42. A method according to claim 41 wherein said interface between the separation device and the mass spectrometer is an electrospray ionization interface.

* * * * *